United States Patent [19]

Albert

[11] 4,057,745
[45] Nov. 8, 1977

[54] SCANNING X-RAY SOURCE

[76] Inventor: Richard D. Albert, 317 Hartford Road, Danville, Calif. 94526

[21] Appl. No.: 663,988

[22] Filed: Mar. 4, 1976

Related U.S. Application Data

[62] Division of Ser. No. 481,954, June 24, 1974, Pat. No. 3,949,229.

[51] Int. Cl.$^2$ ............................................. H01J 35/08
[52] U.S. Cl. ....................................... 313/55; 313/330
[58] Field of Search .................................. 313/55, 330

[56] References Cited

U.S. PATENT DOCUMENTS

| 2,153,586 | 4/1939 | Nicolson | 313/55 X |
| 2,638,554 | 5/1953 | Bartow et al. | 313/55 X |
| 2,730,566 | 1/1956 | Bartow et al. | 178/6.5 |
| 3,271,608 | 9/1966 | Rome et al. | 313/55 X |

Primary Examiner—Rudolph V. Rolinec
Assistant Examiner—Darwin R. Hostetter
Attorney, Agent, or Firm—Phillips, Moore, Weissenberger, Lempio & Majestic

[57] ABSTRACT

Radiographic images of high definition and clarity are produced quickly and with reduced radiation exposure of the subject by utilizing a scanning X-ray source in which a moving point source of X-rays is created by sweeping an electron beam in a raster pattern on a broad anode. A radiation detector having a very small radiation sensitive area is situated on the opposite side of the subject from the source. The output of the detector controls electron beam intensity within a cathode ray type display tube wherein the raster pattern is synchronized with that of the X-ray source to produce an image of internal structure of the subject. In some embodiments of the invention, the small radiation detector is mounted on a probe suitable for insertion into internal regions of a living body or into recesses in mechanical structure to be examined. Stereo images may be produced by employing two spaced apart detectors controlling two separate images which are directed to separate eyes of the observer or by using a single detector alternately controlling each of the two images while the raster pattern at the source is alternately shifted between two at least partially separate areas of the anode. As the detector output is an electronic signal, the image data may be stored on magnetic tape or the like and may also be readily processed by electronic techniques for such purposes as image enhancement, and addition, subtraction or superimposition of images. Automatic brightness control may also be provided to produce uniform contrast in different areas of the image where the corresponding different regions of the subject have different average densities.

9 Claims, 19 Drawing Figures

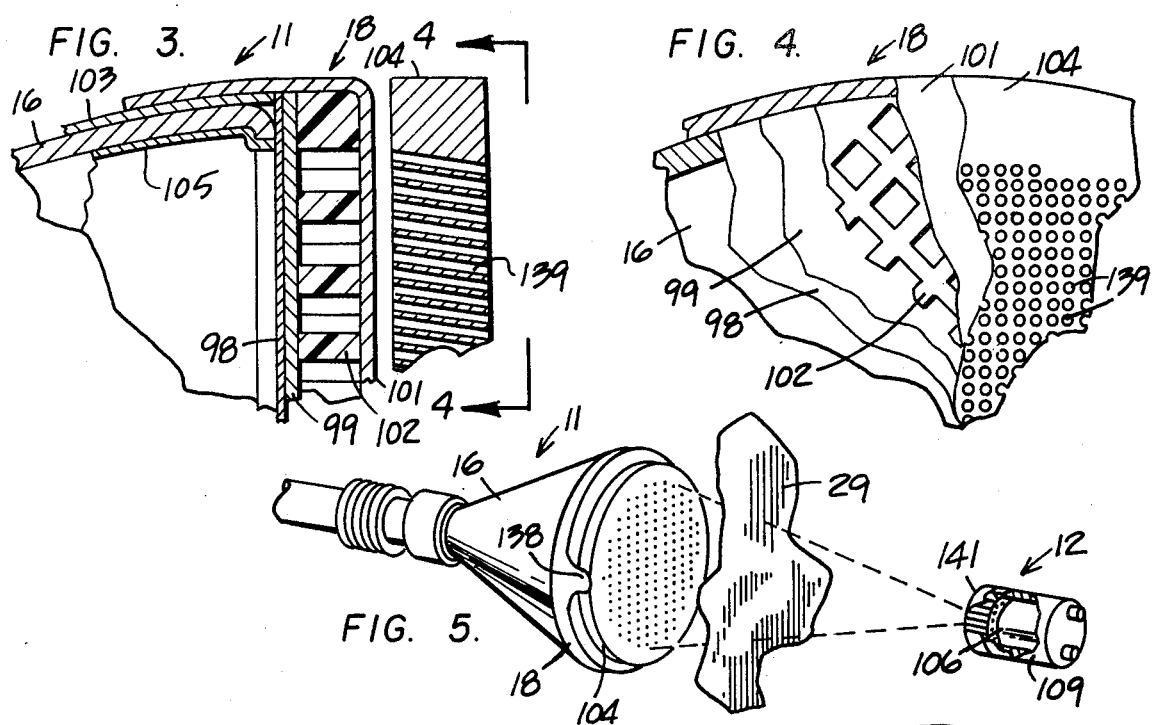
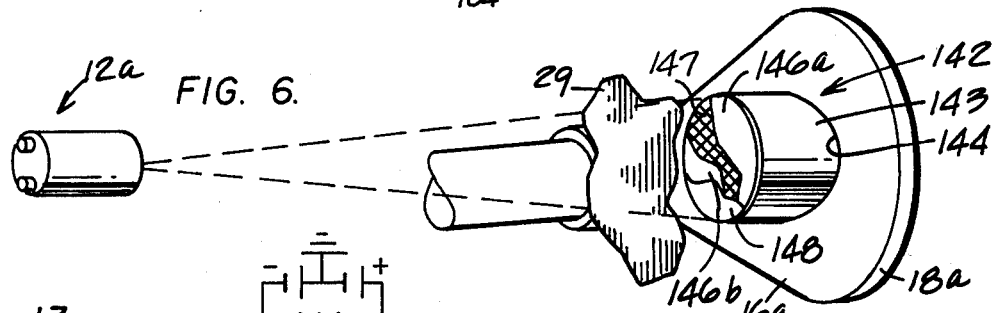
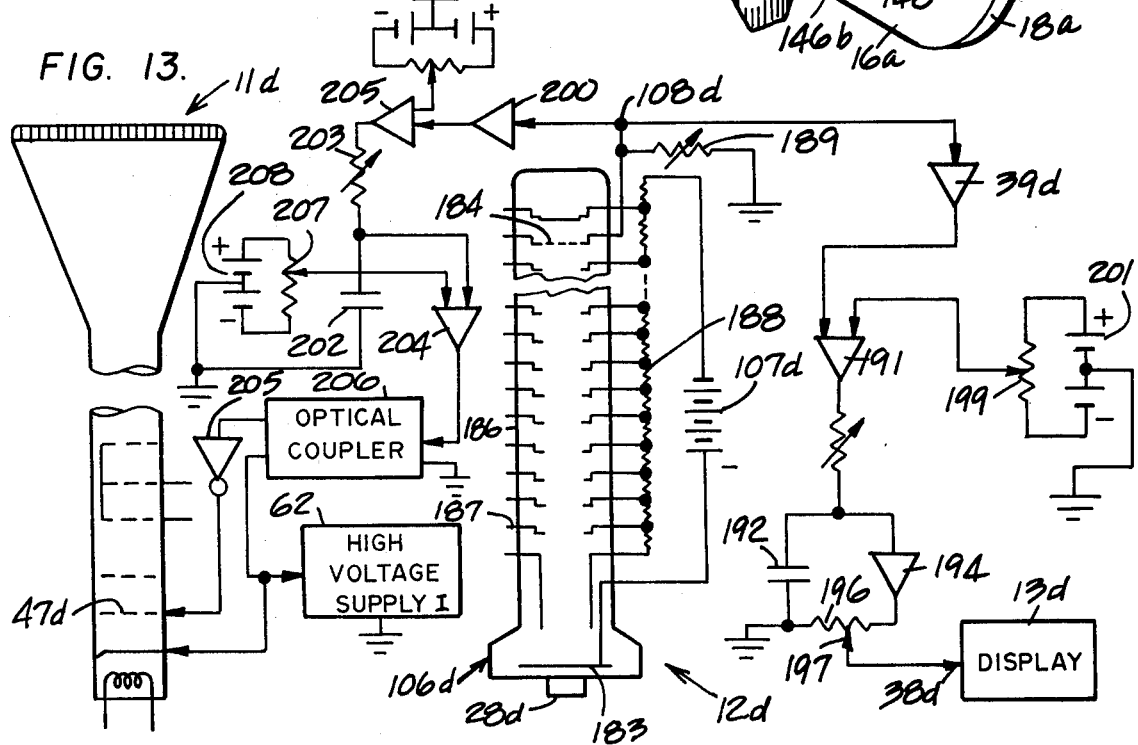

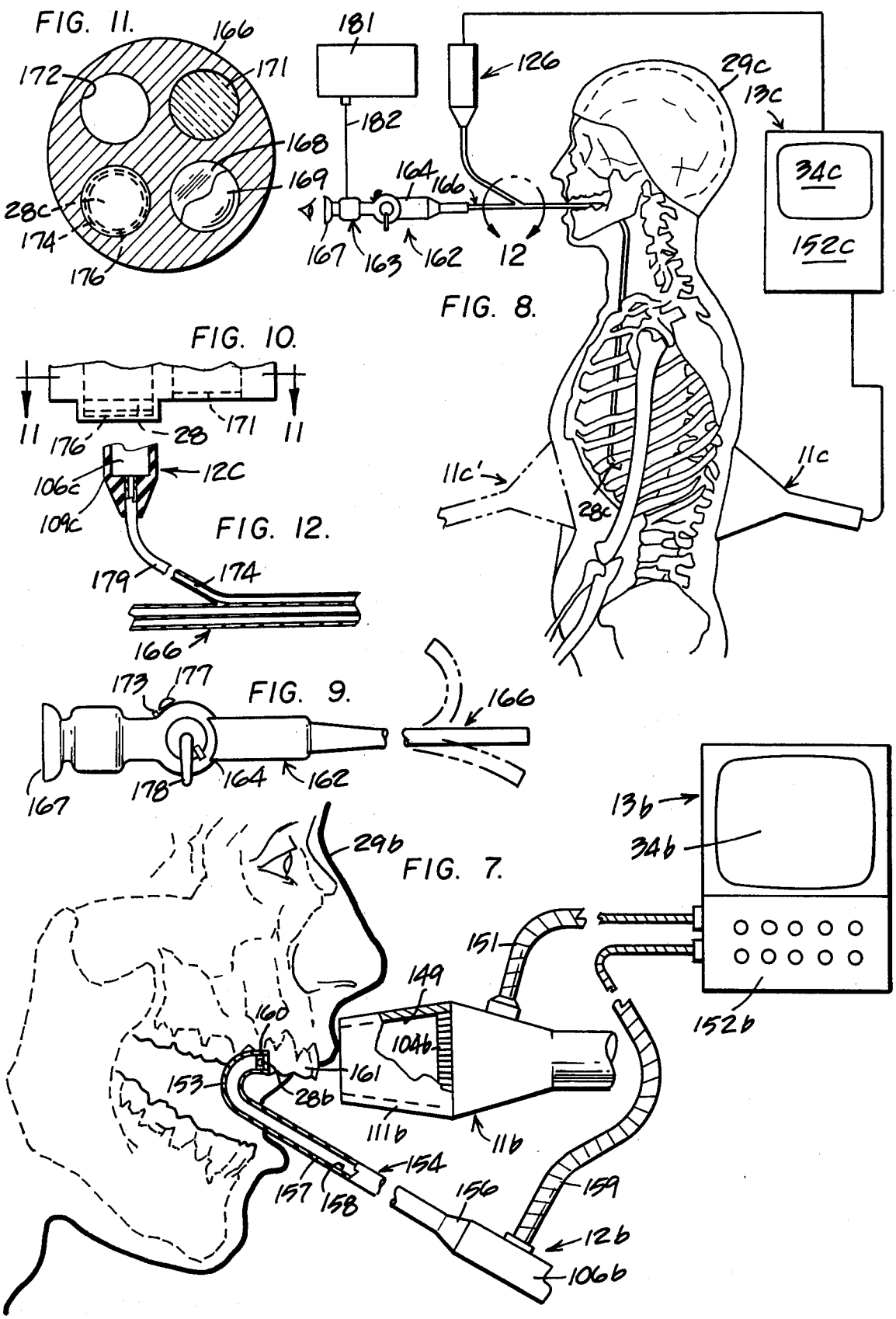

SCANNING X-RAY SOURCE

This is a divisional application of copending application Ser. No. 481,954, filed June 24, 1974 and now U.S. Pat. No. 3,949,229.

BACKGROUND OF THE INVENTION

This invention relates to radiography and more particularly to an improved scanning X-ray system and method for producing image data indicative of internal characteristics of subjects to be examined.

X-ray derived images of living subjects or mechanical structures are most commonly obtained by using an X-ray source in which a small area anode or target is bombarded with accelerated electrons. The resultant X-rays diverge from what may be regarded as essentially a point source. The divergent X-ray beam, usually consisting of a continuous wave-length spectrum, passes through the subject and impinges on a photographic film which must then be developed to produce a visually perceptible image. In other instances, the divergent X-ray beam is received on a broad screen formed in part of a material which fluoresces visible light in response to X-radiation.

There are several characteristics which detract from the utility of X-ray systems of the form discussed above and which tend to limit the quality of the images which are obtained. Most notably, a sizable radiation dosage is required to produce a clear image and this constitutes a potential hazard to operator personnel as well as to an invivo subject. A large proportion of the X-rays which are generated and passed through the subject do not produce a discernible antinic or fluorescent reaction in the film or screen and thus are essentially unutilized. Where photographic film is used, a delay is necessary while the film is being developed. Further, the required equipment tends to be undesirably bulky and heavy and consumes a substantial amount of electrical power. If stereoscopic images are desired, these several undesirable characteristics, including high radiation dosage, are aggravated since much of the equipment must be duplicated for this purpose.

Except in certain special circumstances such as in dental radiology, it is usually a practical necessity to produce an image which includes the full depth of a subject. Because of the necessarily large size of the photographic film or the like, it is often not practical to insert such means into a human body or into convoluted recesses within mechanical structures which are to be examined. However, in many instances more useful data could be obtained by imaging only a portion of the total depth of a subject. Further, the commonly employed X-ray techniques are not susceptible to localized contrast control in different areas of the image except by cumbersome techniques, such as localized partial masking, which are not fully effective and which have undesirable side effects.

Another serious problem in the above-described conventional X-ray system results from the largely unavoidable production of secondary X-rays within the subject being viewed. In order to achieve maximum definition and clarity in the image, all X-rays which react with the film or screen must have a single small area of origin at the source. This is not usually achieved in practice since a certain proportion of the primary X-rays from the source interact with individual atoms within the subject in a manner which causes secondary X-rays to be emitted from within the subject. As these secondary X-rays do not originate at the same point as the primary X-rays, interaction of the secondary X-rays with the film or fluorescent screen degrades the quality of the image. The fact that the film must often be disposed as close to the subject as possible aggravates this problem as this means a large proportion of the secondary X-rays impinge upon the film.

It is a common practice to reduce degradation from secondary X-rays by disposing a focussing grid between the subject and the film or screen. Such a grid is formed of radiation opaque material and has a series of radiation transmissive passages aligned to transmit only X-rays travelling along paths which converge at the X-ray source. The grid may be oscillated to avoid superimposing an image of the grid itself into the image of the subject. Such grids are only partially effective for the desired purpose, may themselves be a source of secondary X-rays, and have the undesirable effect of still further increasing the amount of X-radiation which must be generated to produce an acceptable image.

It is often desired to store records of X-ray examinations, particularly in medical and dental applications, and the physical size, fragility, and cost of X-ray film creates complications in this connection. Further, where X-ray film is used as a data storage medium, complex equipment and operations are required if it should be desired to process the data by electronic image enhancement techniques.

In order to avoid certain of the problems discussed above, it has heretofore been proposed to provide a moving point source of X-rays whereby the subject may be systematically scanned in a raster pattern. The X-radiation passing through the subject may then be detected electronically and displayed on a television or cathode ray tube which has a raster pattern and sweep frequencies coordinated with that of the source. Prior U.S. Pat. No. 2,730,566 describes one such system. A basic advantage of such a system is that electronic radiation detectors can be more sensitive than photographic film or fluorescent screens and therefore the required radiation dosage of the subject may be reduced.

As heretofore designed, such scanning systems do not fully resolve certain of the problems discussed above and have no significant advantage over the more commonly used film technique insofar as others of these problems are concerned. These prior X-ray scanning systems necessarily require a very large area radiation detector which, in effect, replaces the photographic film or fluorescent screen discussed above.

Suitable radiation detectors of the necessary size are not manufactured in quantity by commercial suppliers, and at best are inherently costly and subject to reduced sensitivity and an increased spurious count factor. Further, a large detector cannot usually be inserted into a living body or into restricted regions within apparatus to be examined.

To produce any useful data at all, the prior X-ray scanning systems necessarily require that a broad multiapertured focussing collimator or grid be positioned between the scanning X-ray source and the radiation detector so that the only X-rays counted at any specific instant are those which have passed through one specific region of the subject. This tends to reduce image definition as X-radiation is alternately absorbed within the collimator and then transmitted therethrough many times in the course of each scan, in effect reducing the image to a mosaic of dots.

Although some secondary X-rays may be absorbed in the collimator, many pass through the openings thereof and are counted by the detector as in the more conventional X-ray film process.

For these and other reasons, prior X-ray scanning systems have not replaced the photographic film technique, at least to any great extent, notwithstanding the reduction in radiation dosage which can be inherent in such systems.

SUMMARY OF THE INVENTION

This invention provides a practical, efficient radiographic method and an X-ray system of the scanning form which is capable of producing high clarity image data with reduced radiation dosage of the subject. Considered broadly, the invention utilizes an X-ray generating component wherein a moving point source of divergent X-rays is produced by scanning a broad area target plate with a charged particle beam, in combination with a relatively very small area radiation detector spaced apart from the source to intercept X-rays which have passed through the subject undergoing examination.

The output of the detector may be used to control a cathode ray display tube or the like, having a raster pattern coordinated with that of the X-ray source, to produce a visual radiographic image of the subject. The detector output signals may also be stored on magnetic tape or by other means for later reconstruction as an image and various electronic image enhancement techniques may readily be applied if desired.

The use of a large area source of X-rays in combination with a relatively very small area detector is essentially the reverse of conventional techniques and has pronounced advantages. As extremely sensitive small X-ray detectors are available, the overall radiation dosage of the subject may be greatly reduced.

In addition, image quality is greatly improved by reducing the effects of secondary X-rays thereon. Secondary X-rays generated within the subject may be emitted in all directions. Where the X-ray sensitive surface is large as in conventional systems, a relatively sizable proportion of the secondary X-rays are intercepted and register in the image to degrade the quality thereof. As the detection surface is relatively minute in the present invention, only a relatively very small proportion of the total secondary X-ray emission has such an effect. Thus, definition and clarity are greatly enhanced.

While it is advantageous in some circumstances to provide a multi-apertured collimator between the X-ray source and the detector of the present invention, undesirable secondary X-ray effects are greatly reduced even in the absence of such a collimator and the system is by no means dependent upon the presence of a collimator for operation, as in prior scanning X-ray systems.

As the X-ray detection element is very small, it is susceptible to being situated within the human body or in confined internal recesses of structures to produce images of only selected internal regions thereof. Accordingly, some forms of the invention provide for mounting of the detector on probes suitable for facilitating such operations. Automatic brightness control is provided in some forms of the invention to further reduce radiation dosage and to provide a more uniform contrast throughout different areas of the image by feeding back an averaged image intensity signal to the X-ray source to vary X-ray output in the course of the scanning as required for this purpose. Stereoscopic images may be produced in certain forms of the invention by using two small area X-ray detectors which are spaced apart with each controlling separate visual images that are viewed by separate eyes of the observer or, in another form of the invention, by utilizing a single detector controlling the two separate images alternately wherein the raster pattern area at the X-ray source is alternately shifted between two at least partially separate areas of the target plate of the source.

Accordingly, it is an object of this invention to facilitate the production and analysis of radiographic or fluoroscopic images and image data.

It is another object of this invention to reduce the radiation exposure of subjects and operator personnel while producing X-ray derived image data of extremely high definition and clarity.

It is an object of the invention to reduce the image degrading effects of secondary X-rays in radiographic operations.

It is still another object of the invention to provide for more convenient and reliable storage of radiographic image data and to facilitate the application of electronic image enhancement techniques thereto.

It is an object of the invention to facilitate the production of radiographic or fluoroscopic images taken from viewpoints within the interior regions of living or inanimate subjects.

It is still a further object of the invention to provide an X-ray imaging method and apparatus adaptable to the production of stereoscopic radiographic images without excessive system complication and without requiring substantially increased radiation dosage of the subject.

It is another object of the invention to provide for relatively light, compact, adaptable and more portable radiographic apparatus and to reduce the electrical power consumption in the course of operation of such apparatus.

The invention, together with further objects and advantages thereof, will best be understood by reference to the following description of certain preferred embodiments taken in conjunction with the accompanying drawings.

BRIEF DESCRIPTION OF THE DRAWINGS

In the accompanying drawings:

FIG. 3 is an enlarged section view of a portion of the X-ray source of FIGS. 1 and 2, FIG. 4 is an end view of the structure shown in FIG. 3, taken along line 4—4 thereof, FIG. 5 is a perspective view of the X-ray source and detector assembly for a system similar to that of FIGS. 1 to 4 but including supplementary collimator means to further reduce radiation exposure, to reduce X-ray scattering within the subject and to further reduce detector error from secondary X-rays and from ambient radiation, FIG. 6 illustrates a modification of the X-ray source wherein X-rays emitted in a backward direction from the source are utilized for imaging, FIG. 7 illustrates another embodiment of the system which is particularly adapted for dental applications, FIG. 8 illustrates an adaptation of the system suitable for producing X-ray images of only a portion of the total thickness of a human body or other subject, FIG. 9 is an enlarged view of an endoscope mounted X-ray detector utilized in the system of FIG. 8 in order to produce an image taken from a viewpoint within a living human body, FIG. 10 is an enlarged view of the probe end of the endoscope of FIG. 9, FIG. 11 is a cross section view through the probe end of the endoscope of FIGS. 8, 9 and 10 taken along line 11—11 of FIG. 10, FIG. 12 is an enlarged section view of the area of FIG. 8 encircled by dashed line 8 thereof, FIG. 13 is a circuit diagram illustrating modifications of the electrical control circuits of FIG. 2 to adapt the system for operation on a continuous detector signal basis, instead of a pulse basis, and to include automatic brightness control for providing a more uniform contrast throughout the various areas of the visual image.

DESCRIPTION OF PREFERRED EMBODIMENTS

Figure 1:
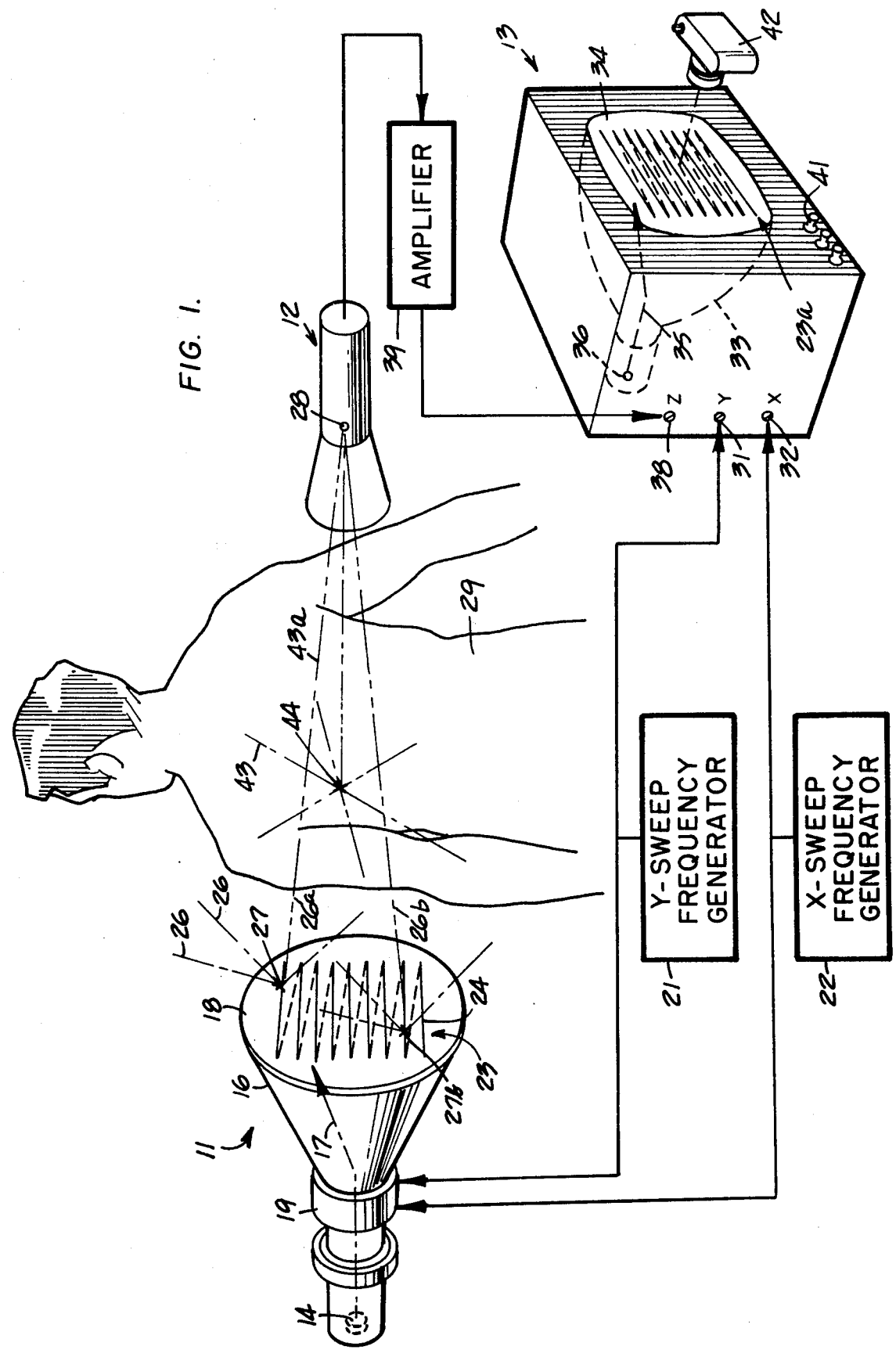
FIG. 1 shows an X-ray source, detector and image display means as utilized in the practice of the invention to produce a visible image or internal regions of a subject.

Referring initially to FIG. 1 of the drawings, a scanning X-ray system in accordance with the invention includes a scanning X-ray source 11, an X-ray detector assembly 12 and a visible image producing means which may be a cathode ray tube 13 or other X-Y display device. An exterior perspective view of these components is shown in FIG. 1 to facilitate an understanding of the basic method of operation of the invention, the internal construction of the source 11 and detector 12 and suitable control circuits being hereinafter described.

The X-ray source 11 may be essentially a cathode ray tube of the form having a cathode 14 at one end of an evacuated tube or envelope 16 from which electrons are accelerated in a beam 17 towards a broad anode or target plate 18 at the opposite larger end of the envelope. Beam deflection means such as a magnetic beam deflector coil assembly 19 is controlled by a Y axis sweep frequency generator 21 and an X axis sweep frequency generator 22 causing the electron beam 17 to scan the inner surface of target plate 18 in a raster pattern 23 wherein the point of impact of the electron beam on the target plate is sequentially swept along a series of parallel spaced apart substantially linear scan lines 24. The scan lines 24 as depicted in FIG. 1 are fewer in number and more widely spaced apart than is generally the case in practice in order to more clearly illustrate the method of operation and it should be understood that a considerably larger number of more closely spaced scan lines 24 are present in actual practice. The area of raster 23 is usually limited to that necessary for scanning the region of interest within the subject to avoid unnecessary radiation exposure.

Although the electron beam forming, accelerating and controlling means of the source 11 need not necessarily differ from those of known cathode ray tubes except insofar as higher beam accelerating voltages may be required, the structure of the anode or target plate 18 does differ from that of prior tube configurations. In particular, the target plate 18 is formed at least in part of a material such as copper, for example, which readily emits X-rays 26 upon being bombarded by high energy electrons.

In operation, X-rays are emitted from the target plate 18 and at any given instant the emitted X-rays originate at a single minute small area 27 at the face of the source 11 which area progressively moves along each of the scan lines 24 of the raster pattern 23. The X-rays 26 at any given instant are emitted in all directions from point of origin 27. Thus source 11, in effect, provides a moving point source of X-rays.

The X-ray detector 12 may be any of several known forms of detector which produce an electrical output signal indicative of individual X-rays or of the quantity of X-rays impinging on a radiation sensitive area 28. Scintillation detectors are one such form of radiation detector and ionization chambers or various solid state detectors or the like may also be adapted for the present invention. Regardless of the type of X-ray detector 12 which is employed, the radiation sensitive area 28 of the detector should be substantially smaller than the area of the raster pattern 23 of X-ray source 11. Preferably, the sensitive area 28 of the detector should be as small as possible in relation to raster pattern 23, with due regard to obtaining an adequate response from the acceptable radiation flux level, as the difference in the size of sensitive area 28 and that of raster pattern 23 is an important factor in determining definition in the visible image which is obtained.

The X-ray detector 28 is spaced apart from the X-ray source 11 in order that the subject 29 to be examined may be disposed between the source and detector in the path of X-radiation travelling from the source target plate 18 towards the sensitive area 28 of the detector. While the subject 29 as depicted in this example is a living person to be X-rayed for medical purposes, the system is equally applicable to examination of inaminate subjects. For example, it is often desired to obtain a radiographic image of castings or other structural components for machinery to determine if there are internal flaws. Similarly, is sometimes necessary to conduct an X-ray examination of the luggage of airline passengers for security purposes and many other circumstances are known to the art in which it is desirable to provide a radiographic image of living or inanimate objects.

The system may operate on either a pulse basis or on a continuous signal basis depending on the general level of the radiation flux transmitted through the subject and received by the detector 12. If the radiation flux level produced by the source 11 is kept sufficiently low that simultaneous receipt of a number of X-rays at the detector 12 is infrequent, then the detector may be of the form producing a discrete output pulse for each individual detected X-ray. If the X-ray flux output of the source 11 is higher so that there are normally a sizable number of individual X-rays being received by the detector 12, then the detector may be of the form which produces a more or less continuous output signal having a voltage, current, or in some instances a frequency, proportional to the instantaneous magnitude of detected X-radiation.

The visible image producing display means 13 may include a cathode ray tube display device 33 of the known form that is similar in many respects to the previously described X-ray source 11 except insofar as the anode at the large end of the tube is a screen 37 formed in part of a phosphor material which emits visible light in response to bombardment by the internal electron beam 34 emitted from the cathode 36 at the opposite end of the tube. While cathode ray tubes of the oscilloscope type provide better image definition, a commercial television receiver set may also be used as the display means 13 if the sweep and intensity control signals from external elements of the present system are processed through a video scan converter.

By coupling the sweep frequency generators 21 and 22 to the sweep frequency terminals 31 and 32 of the cathode ray tube, the electron beam 34 is caused to scan screen 37 in a raster pattern 23a similar to the raster pattern 23 of the X-ray source 11. Thus at any given instant, the point of impact of electron beam 34 of the display means on phosphor screen 37 corresponds with the point of impact of the electron beam 17 of the source on target plate 18 thereof.

The output signals from X-ray detector 12 are transmitted to the Z or beam intensity terminal 38 of the cathode ray tube through an amplifier 39. Thus, the intensity of the electron beam 34 striking the phosphor screen 37 of the display means at any given time is determined by the X-ray flux received at detector 12 at that time. The degree of brightness of each point on the screen 37 as perceived by an observer varies in accordance with the variations of the radiation flux intercepted by the detector 12 at successive periods in each scan of the subject 29.

Accordingly, the electron beam 34 of display tube 33 produces a point of light on phosphor screen 37 which moves in a pattern corresponding to the pattern of movement of the electron beam 17 on target plate 18 of the X-ray source 11. As the brightness of each successive point in the visible image on screen 37 is determined by the X-ray transmissiveness of a corresponding separate portion of the subject 29, the visible image as perceived by a viewer is a radiograph of the region of the subject situated between source target plate 18 and detector 12. Using the system as described above, relatively radiation transmissive regions of the subject, such as soft invivo tissue, will appear bright in the visible image while relatively radiation opaque regions such as those containing bone will appear dark in the visible image. If it is desired to reverse this in order to obtain a negative image similar to conventional photographic X-ray films, this is readily accomplished by inverting the detector output signal in amplifier 39. The apparent size of structure within the subject as perceived in the image may be varied by moving the subject closer to the detector or further away therefrom. If it is desired to form a visible image on the basis of a single scan of a subject or a limited number of scans, the visual display means 13 may be of the form having a persistence control 41 for retaining a visual image on the screen 37. Although other highly advantageous means for storing a record of the examination will be hereinafter described, the visible image on screen 37 may be recorded photographically if desired by a camera 42.

Considering now certain significant characteristics of the system from the standpoint of reducing radiation dosage and increasing definition and clarity of the visual image, it is possible to operate on the basis of a lower overall radiation dosage of the subject 29 than is the case when using conventional photographic detection of the X-ray image. One reason for this is that electronic or solid state radiation detectors 12 are in general far more sensitive to radiation than is photographic film. Electronic detectors of this kind are available which are capable of registering virtually each individual X-ray which impinges on the sensitive area 28. Only a relatively small proportion of the X-rays passing through a conventional photographic film emulsion produce an actinic reaction that contributes to the production of a visible image.

With regard to the matter of definition in the visible image, it should be observed that while X-rays are emitted in all directions from the point of impact 27 of the electron beam on target plate 18 of the source, only X-rays travelling along a single specific trajectory 26a at any instant reach the sensitive area 28 of the detector and contribute to the visible image. This trajectory 26a subtends a very minute cross-sectional area of the subject 29. This continues to be true as the point of X-ray origin 27 moves along the raster 23, to point 27b for example, although the region of the subject which is intercepted by the detected X-rays is progressively shifted to cover the entire area of interest.

In conventional X-ray processes using a relatively large photographic film, fluorescent screen or a broad electronic radiation detector for the purpose of detecting X-rays transmitted through the subject, serious degradation of the visible image results from the effects of scattered X-rays and secondary X-rays. Secondary X-rays 43 are produced within the subject 29 when a primary X-ray 26 from the source interacts with an individual atom within the subject to cause X-ray fluorescence. Fluorescent secondary X-rays may then be emitted randomly in any direction from the point of origin within the subject as indicated by lines 43 in FIG. 1. A broad area film, fluorescent screen or radiation detector will, simply because of its expanse, intercept and record a large proportion of these randomly directed X-rays 43 particularly since it is usually desirable to dispose such means as close to the subject as possible. These recorded scattered or fluorescent X-rays do not originate at the focal point of the conventional X-ray system and therefore introduce much erroneous information into the visual image.

Secondary X-rays 43 can have relatively very little effect on the visible image in the present system. Because of the small size of the sensitive area 28 of the X-ray detector 12, only a minute proportion of the total secondary X-ray radiation 43 can be intercepted and recorded by the detector, specifically only X-rays which are travelling along a single trajectory 43a of minute cross-section for any given point of origin 44. Further, it is not a necessity nor usually even desirable, that the detector to be located immediately adjacent the subject 29 in an arrangement which would cause the sensitive area 28 to intercept a relatively larger proportion of the secondary X-radiation 43. In contrast to conventional systems, it is usually more desirable that the subject be situated closer to the source 11 and more remote from the detector 12, so that the scan intercepts a larger region of the subject and to minimize distortion resulting from the depth of field of the subject.

Figure 2:
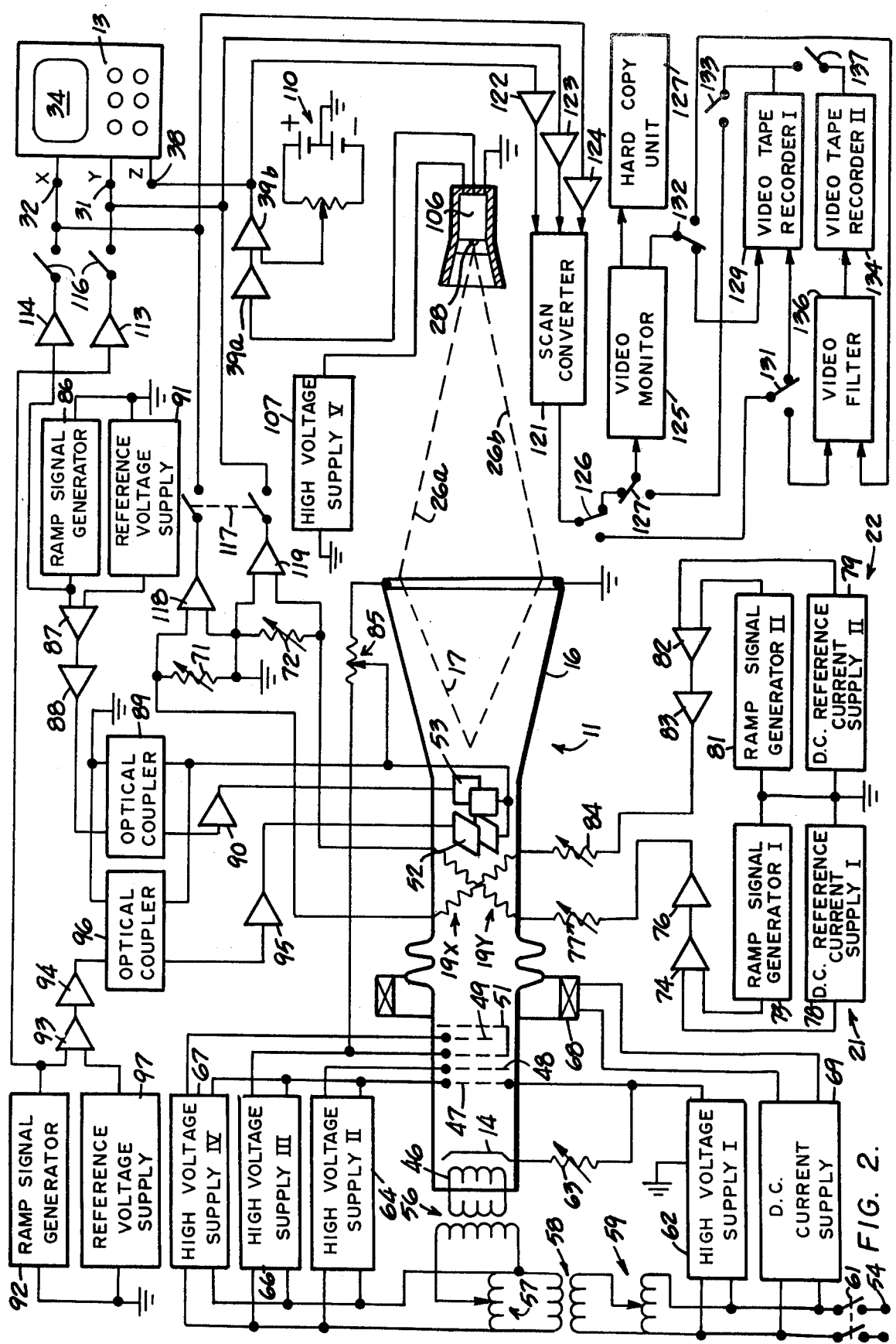
FIG. 2 is a schematic circuit diagram of the apparatus of FIG. 1 together with control circuits therefor and signal processing and storage circuits which may be used therewith.

Referring now to FIG. 2, suitable internal constructions for the X-ray source 11 and detector assembly 12 are shown together with control circuits and accessory equipment.

As previously described, the X-ray source 11 may have a vacuum envelope 16 with an electron emissive cathode 14 at one end and a thin flat target plate or anode 18 at the opposite larger end. In the present example, the anode or target plate 18 is maintained at ground potential to minimize arcing problems. Source 11 has a filament 46 for heating cathode 14 to cause electron emission and has a control grid 47, a first anode 48 and a focussing grid 49 which is nested between elements of a double gridded second anode or ultor 51, such elements being spaced apart and being progressively more distant from the cathode 14 for the purpose of accelerating and focussing electrons into a beam 17 directed towards the target plate 18. In order to systematically deflect the electron beam to produce the desired scanning action, the previously described magnetic deflection coil assembly 19 is disposed coaxially around envelope 16. Beam deflection may also be accomplished with spaced apart pairs of Y and X electrostatic deflection plates 52 and 53 respectively. As is understood by those skilled in cathode ray tube art, either the magnetic or the electrostatic beam deflection means may be used separately or the two may be used in combination.

To supply current to filament 46, opposite ends of the filament are coupled to AC power line terminals 54 through a step down tansformer 56, a first autotransformer 57 for regulating filament power, an isolation transformer 58, another autotransformer 59 and an on/off switch 61. Transformer 58 isolates the high voltage end of the source from ground while the second autotransformer 59 enables simultaneous adjustment of filament current and the voltages of the anodes 48 and 49 and ultor 51 to control the magnitude and energy of the electron beam 17.

A first high voltage supply 62 applies positive voltage directly to control grid 47 and indirectly to cathode 14 through a variable resistor 63. Resistor 63 enables adjustment of the bias voltage between the control grid and the cathode and also acts to stabilize the cathode current since an increase in cathode current drives the control grid more negative thereby tending to return the cathode current to the original value. Second, third, and fourth high voltage supplies 64, 66, and 67 respectively, each coupled to the AC power terminals 54 through isolation transformer 58, supply adjustable positive voltages to first anode 48, ultor 51, and focussing grid 49 respectively, these voltages being referenced to that of the control grid. As is understood in the art, the voltage applied to ultor 51 is usually considerably higher than that applied to the other elements at the cathode end of the source so that the beam deflection amplitude will be less sensitive to the overall accelerating voltage between the cathode 14 and the final anode which in this instance is the target plate 18. To provide further focussing of the electron beam, a focussing coil 68 is disposed coaxially around the envelope 16 in the region between ultor 51 and deflection coils 19. Focussing coil 68 is energized by an adjustable DC current supply 69 which is coupled to the AC power lines through on/off switch 61.

Thus, the above described elements act to form and direct an electron beam along the axis of envelope 16 towards target plate 18 and the magnitude, energy and cross-sectional area of the electron beam are electrically controllable within limits. The electron beam 17 may be caused to undergo the previously described scanning action on target plate 18 by utilizing either the magnetic deflection coils 19 or the electrostatic deflection plates 52 and 53 or a combination of both.

To control the magnetic deflection coils 19, one side of both the X and Y deflection coils 19x and 19y respectively is coupled to ground through separate variable resistors 71 and 72 respectively. The other side of X deflection coil 19x receives a current, which progressively rises and then drops abruptly in a repetitive manner, from a first ramp signal generator 73 which is coupled to the coil through a differential amplifier 74 and an adjustable gain amplifier 76 and variable resistor 77. The other input to differential amplifier 74 is determined by a first adjustable DC reference current supply 78. The width and height of the raster pattern may be determined by adjusting the wave form amplitude from ramp signal generator 73 and by adjusting the gain of amplifier 76. The DC reference current supply 78 enables control of the position of the raster pattern on target plate 18 in the Y direction. If only magnetic beam deflection is being used, then the position of the electron beam on target plate 18 in the Y direction at the start of each raster is determined by the magnitude of the current from the reference current supply 78.

Current is supplied to the X axis deflection coil 19x by a similar arrangement of deflection control components including a second DC reference current supply 79, a second ramp signal generator 81, a second differential amplifier 82, a second adjustable gain amplifier 83 and another variable resistor 84 with these components being interconnected in the manner described above for the Y axis magnetic deflection control system.

Similarly, to provide X axis sweep frequencies for the electrostatic beam deflection system, one X and one Y deflection plate is maintained at a selectable voltage between that of the ultor 51 and ground by connection to the adjustable tap of a potentiometer 85 which has a resistive element connected between the ultor and ground. A third ramp signal generator 86 is coupled to the other X axis deflection plate 53 through a differential amplifier 87, variable gain amplifier 88, an optical coupler 89 and driver amplifier 90. Optical coupler 89, which has an output referenced to that of the potentiometer 85, serves to isolate the ramp signal producing components from the high voltage at the deflection plates. An adjustable reference supply 91 is coupled to the other input of the differential amplifier 87 to provide for selection of the X direction position of the electron beam in the absence of an output from ramp signal generator 86 so that by adjustment of the reference voltage and the ramp signal amplitude, the position and extent of the raster pattern on target plate 18 may be shifted in the X direction as desired. To control Y axis deflection in the electrostatic system, a fourth ramp signal generator 92 is coupled to the other Y deflection plate 52 through another differential amplifier 93, an adjustable gain amplifier 94, and another optical coupler 96 and driver amplifier 95. To provide for selective shifting of the raster pattern on target plate 18 in the Y direction, another reference voltage supply 97 is coupled to the other input of differential amplifier 93.

Considering now suitable detailed structure for the target plate 18 of the source 11, reference should be made to FIGS. 3 and 4 in conjunction. The primary target substance from the standpoint of producing X- rays is a thin layer 98 of suitable metal such as copper which may be vacuum deposited against a backing plate 99 of relatively low atomic number metal such as aluminum. An additional plate 101 of similar low atomic number material is spaced from plate 99 and a multi-apertured or honeycomb structure 102 of X-ray transmissive material such as plastic is disposed therebetween. Plates 99 and 101 and the included honeycomb structure 102 serve to support the thin layer 98 of target material and provide a high strength closure for the face of the vacuum region of the X-ray source. The insulative envelope 16 of the source is provided with grounded conductive coatings 103 and 105 on the forward portions of the exterior and interior surfaces respectively and such material is in electrical contact with the copper layer 98. A collimator element 104 situated adjacent plate 101 may be utilized in certain instances to further reduce radiation dosage of the subject and to increase clarity of the image and will hereinafter be described in more detail.

Considering now suitable structure for the X-ray detector 12, with reference again to FIG. 2, the radiation sensitive area 28 of the detector is defined by a small scintillation crystal which may be thallium doped sodium iodide for example although other suitable scintillator materials are known to the art. The crystal 28 is optically coupled to a photomultiplier tube 106 which is energized by a high voltage supply 107 and which has an output conductor 108 for transmitting electrical pulses in response to X-rays received at the sensitive area 28. Phototube 106 and the crystal forming the radiation sensitive area 28 are disposed within a housing 109 which is preferably thick and formed of a relatively radiation opaque material such as lead in order to shield the internal elements of the detector from stray background radiation. Preferably, a cone 111 formed of such radiation opaque material extends from housing 109 a short distance towards X-ray source 11 and has a tapered internal passage subtending the target plate 18 area of the X-ray source in order to shield the radiation sensitive area 28 from radiation arriving from directions other than that of the X-ray source 11.

A thin plate 112 formed of a material such as aluminum which is relatively transmissive of X-rays but opaque to visible light is disposed transversely within cone 111 to block visible light from the scintillation crystal at the radiation sensitive area 28.

The output signal from detector 12 may be stored for later display or otherwise processed as will hereinafter be described in more detail, but in this example of the invention, such signal is transmitted to the display means 13 to provide an instantaneous radiograph of a subject situated between the source and detector. For this purpose, the output 108 of the photomultiplier tube 106 is coupled to the Z or beam intensity terminal 38 of the display means 13 through a pre-amplifier 39a and an additional differential amplifier 39b. The other input of amplifier 39b receives a reference voltage, from a source 110, which may be adjusted to eliminate small amplitude signals from tube noise and the like. If the system is to be operated in the pulsed mode where individual X-rays produce individual pulses at the output of photomultiplier 106, amplifier 39b is operated in the saturated mode whereby the pulse signals supplied to visual display means 13 are of nearly uniform amplitude. If desired, the detector output signals in the pulse mode of operation may be differentiated or clipped by means known to the art to reduce the duration of such signals thereby increasing the ability of the system to respond to X-rays which are received in rapid succession. If the system is operated with a higher radiation flux where the photomultiplier tube 106 produces a more or less continuous output signal having a current level proportional to the instantaneous magnitude of radiation flux intercepted by radiation sensitive area 28, then the amplifier 39 is a wide band amplifier or video amplifier and amplifier 39b is unnecessary.

In order to produce a visible image on the screen 37 of the display means 13, the raster pattern of the display 13 must be synchronized with that of the source 11. For this purpose, the Y axis electrostatic deflection signal of the X-ray source, taken from the output of ramp signal generator 92, may be transmitted to the Y sweep frequency terminal 31 of the visual display 13 through an isolation amplifier 113. The X axis electrostatic deflection signal of the source from generator 86 may be transmitted to the X sweep frequency terminal 32 of the display through a second isolation amplifier 114. To selectively, connect and disconnect the electrostatic deflection system of the source with that of the display 13, switches 116 may be connected between ramp signal generators 92 and 86 of the X-ray source and isolation amplifiers 113 and 114. The scanning action of the display means 13 may be synchronized to the magnetic deflection system of the X-ray source 11 by closing another double pole switch 117 to connect the outputs of a pair of differential amplifiers 118 and 119 to the X and Y sweep frequency terminals 32 and 31 respectively of the display means. Amplifier 118 has a pair of inputs connected to opposite sides of the previously described variable resistor 71 while amplifier 119 has a pair of inputs connected across the previously described variable resistor 72.

Accordingly, the scanning raster of visual display 13 is synchronizable with that of the source 11 and since the brightness appearing on display screen 37 at each successive area in the raster is determined by the amount of X-rays received by detector 12 during the corresponding time period of the raster, a visible radiograph of a subject situated between the source and the detector is presented on screen 37.

It has been pointed out that a permanent record of the radiograph may be made by photographing the screen 37 of visual display 13. However, the present system is uniquely adapted to other and in many ways more advantageous image storing and processing means. In particular, the X and Y deflection signals indicate position in the raster pattern and the Z or intensity signal represents image density at each position therein. Through isolation amplifiers 122, 123 and 124 respectively these signals may be transmitted to a scan converter 121 of the form widely utilized in the television industry and which converts such data to video signals suitable for storing and processing by video techniques. The video signal output of scan converter 121 may, for example, be transmitted to a video monitor 125 which produces a visible display therefrom and which may in turn operate a hard copy unit 127 of the known form which prints a copy of an image displayed on the monitor. For this purpose, the output of the scan converter 121 may be transmitted through a first two-position switch 126 to another two-position switch 127 coupled to the input of the video monitor. Alternately, switch 126 may be operated to another position at which the output of the scan convertor 121 is transmitted to a first video tape recorder 129 through another two-position switch 131 for storage on magnetic tape. Tape recorder 129 may also be used to store an image which has been displayed on monitor 125 in the manner previously described as still another two-position switch 132 provides for coupling the output of the monitor to the input of the tape recorder. When it is desired to view or print an image stored on magnetic tape, the output of recorder 129 may be coupled to the monitor 125 by adjustment of another two-position switch 133 and the previously described monitor input switch 127 to couple the output of the recorder to the input of the monitor. Magnetic tapes or the like containing image data may be removed from the recorder and stored for future reference.

Because the system is adaptable to conversion of the radiographic data to video signal form, the various known video techniques for enhancing, superimposing, and otherwise processing video images to develop desired characteristics in an image may readily be utilized. For example, a second video tape recorder 134 may have an input coupled to the output of a video signal filter 136 of the form which can modify the frequency spectrum of the video signal representing the raw image data by emphasizing or de-emphasizing desired parts of the video frequency spectrum. For this purpose, the previously described switch 131 has an alternate position which transmits the output of scan converter 121 to the input of video filter 136 provided switch 126 is also operated to the alternate position. An alternate input to filter 136 is provided by operating the previously described switch 132 to the second position whereby the filter receives the video signal from the output of monitor 125 thereby enabling the image to be viewed prior to filtering and recording. When the processed image stored in video tape recorder 134 is to be viewed, switched 137 and 133 are operated to the alternate positions to transmit the recorder output signal to monitor 125.

It may be observed that the system provides for superimposition of two different images for simultaneous viewing on monitor 125 in instances where this is desirable, such as in medical arteriographic procedures where an image of a patient may be made before and after injection of a contrast agent into the arteries. The first image may be stored in recorder 129 and the second image may be stored in recorder 134. Both images may be simultaneously displayed on monitor 125 in a superimposed relationship by closing switches 133 and 137 with video monitor input switch 127 being in the alternate position. Further, it will be appreciated that individual tapes containing recorder images may be removed from the recorders 129 and 134 for convenient storage and may be replaced in the recorders when it is desired to reconstruct the image at some later time, thereby avoiding many of the problems heretofore encountered in storing large fragile photographic X-ray radiographs.

Prior scanning X-ray systems use a radiation sensitive means, such as a photographic film or a broad detector, that has an extent comparable to that of the face of the X-ray source and this necessarily requires an X-ray collimation element between the source and detector in order to produce any meaningful image. This is not true of the present system which produces a high definition image in the absence of any form of collimator. However, in some circumstances, such collimation means may be advantageously employed in the present system for further reducing radiation dosage of the subject or for further enhancing clarity of the image or for both purposes. Referring now to FIG. 5, a source collimator element 104 may be situated between the X-ray source 11 and the subject 29 to be examined.

The collimator element 104 may, if desired, be mounted on source 11 for example by brackets 138 extending forward from target plate assembly 18 at opposite sides of the collimator element. Referring now again to FIGS. 3 and 4 in conjunction, the collimator element 104 is formed of a relatively X-ray absorbent material such as lead or steel coated with a layer of gold and has a large number of linear apertures 139 extending therethrough and directed towards the subject and X-ray detector. X-rays emitted from the target elememt 98 of the source tend to be absorbed in the collimator 104 except for the particular portion of the X-rays which are directed towards the detector and are therefore useful for creation of the desired visible image. While the apertures 139 can simply extend transversely through the collimator 104 in parallel relationship with each other if the collimator is sufficiently thin in proportion to the width of the individual apertures, the apertures are preferably slightly non-parallel so that the axes of all apertures converge on the radiation sensitive area of the detector. The effect of the source collimator 104 in absorbing radiation that is not directed towards the detector is useful not only for the purpose of reducing radiation dosage of the subject but also may add clarity and definition to the detected image since in the absence of the collimator a certain proportion of the unutilizable radiation would be scattered in the subject and would thereby be redirected to the detector to introduce erroneous information into the image. If it is desired to reduce any tendency for an image of the collimator 104 itself to appear in the visible image, the collimator may be reciprocated in a direction parallel to the target plate 18 of the source during the course of the examination of the subject.

Referring again to FIG. 5, an essentially similar but normally smaller collimator 141 may be situated between the subject 29 and the X-ray detector 12, the detector collimator 141 in this instance being secured directly to the end of the detector housing 109 which faces the subject. Unlike the source collimator 104, the detector collimator 141 has no direct effect in reaching reducing radiation dosage of the subject 29 but adds clarity to the visible image by eliminating scattered X-rays, secondary X-rays, and background radiations such as cosmic rays which might otherwise reach the sensitive area of the detector.

In the examples of the invention described with reference to FIGS. 1 to 5, the X-rays utilized for creation of the visible image data are the X-rays emitted in the forward direction from the source 11. When the electron beam strikes the inner surface of the target plate element, two distinctive forms of X-radiation are produced. The first form is bremmstrahlung which is a continuous spectrum of many wave lengths and the second form is characteristic X-rays which have one or more specific wave lengths characteristic of the particular material against which the electron beam impacts. In the system of FIGS. 1 to 5, the X-radiation directed forwardly from the face of the tube towards the subject and the detector tends to be at least somewhat monochromatic due to the filtering action of the material of the target plate assembly itself which tends to absorb much of the bremmstrahlung. This effect has the advantage of enabling usage of a somewhat monochromatic X-ray flux having a peak energy determinable by selection of the source target material and by adjustment of electron beam accelerating voltage. Use of a nearly monochromatic X-ray beam has the benefit of reduced patient dosage and a reduced possibility of harmful effects upon a medical patient or the like. However, under some circumstances, it may be preferable to conduct the examination of an object with the wide spectrum bremmstrahlung X-radiation. Referring now to FIG. 6, this may be accomplished in the present system by utilizing the X-radiation which is emitted backwardly from the target plate assembly 18a of the X-ray source 11a and which is therefore not subjected to the filtering action of the material of the target plate assembly. For this purpose, the X-ray detector 12a is situated to the rear of the source 11a and slightly to one side of the axis thereof, that is, the detector is situated on the same side of target plate 18a as the cathode end of the source. The subject 29 to be examined is positioned between the detector 12a and target plate assembly 18a. If the source tube envelope 16a is made of low atomic number metal or glass, much of the backwardly emitted bremmstrahlung radiation will pass therethrough but it is preferable to provide a thin window assembly 142 in the sidewall of the source to assure maximum X-ray transmission in the direction of the detector 12a. The thin window assembly may consist of a cylindrical sleeve 143 extending from a conforming opening 144 in the sidewall of envelope 16a. Sleeve 143 is closed at the outer end by a pair of transverse spaced apart aluminum plates 146a and 146b having a strengthening multi-apertured honeycomb plastic framework 147 situated therebetween. If desired, a low energy X-ray filter layer 148 may also be disposed transversely within sleeve 143 to remove the low energy X-rays which may not contribute significantly to formation of a visible image but may be injurious to a subject.

The system of the present invention is far more adaptable to usage in constricted spaces than are prior systems using films or other extensive elements as a radiation detection medium. FIG. 7 depicts a modification of the system for usage in the form of apparatus particularly adapted for dental X-ray procedures.

The X-ray source 11b may be essentially similar to that previously described except that for dental usage it may be preferable to miniaturize the source relative to one used for general purpose radiology in medical or other applications. Unnecessary radiation dosage of the dental patient 29b may be prevented by securing a conical shield 111b at the face of the source, the shield being formed of radiation absorbent material and having a conical passage 149 of progressively diminishing diameter outward from the face of the tube. Ease of usage and patient comfort is facilitated by supporting the source 11b on a bendable but semi-rigid goose neck support tube 151 having one end coupled to stationary structure which in this instance is the console housing 152b containing the electrical circuits required for the source and detector and containing the visual display means 13b.

To facilitate positioning of the scintillation crystal 28b of the X-ray detector 12b in constricted positions such as within the mouth of the patient 29b, the crystal is disposed at a curved end 153 of a long narrow probe structure 154 which extends from a photomultiplier tube housing 156. Probe 154 may be comprised of a support sleeve 157 formed of a material opaque to visible light and a light pipe 158 extending through the sleeve and being formed of a material which transmits visible light or the other frequencies produced within scintillation crystal 28b in response to X-rays. The scintillation crystal 28b is mounted upon the end of light pipe 158 and optically coupled thereto. To shield the scintillation crystal from ambient light, an X-ray transmissive diaphragm 160, opaque to visible light, is disposed transversely within the curved end of sleeve 157.

A second semi-rigid but bendable goose neck support tube 159 is attached at one end to the detector housing 156 and at the other end to the control circuit console 152b. The electrical control circuits, signal detection circuits nd image display circuit may be similar to that previously described with respect to the first embodiment of the invention, the electrical conductors necessary to interconnect the source 11b and the detector 12b with the associated circuits, preferably being disposed within the bendable support tubes 151 and 159 respectively.

In operation, the X-ray source 11b is positioned to direct X-rays through the particular region of the subject 29b to be examined which in this example are teeth 161. The source support tube 151 may be bent into various positions as necessary to enable the source to be disposed at the desired position but is sufficiently rigid that the source is held stationary at the selected position once this operation is completed. Probe 157 may then be inserted into the patient's mouth, by bending of the probe support tube 159, to position the scintillation crystal 28b at the focal point of the X-ray source and on the opposite side of teeth 161 therefrom. Once positioned in this manner, probe support 159 is sufficiently rigid to retain the scintillation crystal 28b stationary at the desired point. The system may then be operated as previously described to produce a visible image of the teeth 161 on the display means 13b. It will be appreciated that the probe 157 need not be inserted in the patient's mouth in all instances depending on the particular tooth to be examined and the angle of view thereof. Further, while the embodiment of FIG. 7 has been described with reference to dental X-ray procedures, it will be apparent that it has utility in other situations where it is desired to obtain a radiograph of less than the entire thickness of an object and passages are present whereby the probe may be inserted into the interior of the objects. While the goose neck supports for the source 11b and the detector 12b are highly advantageous, it will be apparent that other means can be used for maintaining the source and detector in position. Similarly, the probe 154 may have various configurations other than that depicted in FIG. 7 depending upon the nature of the cavity into which the probe may be inserted.

FIG. 8 depicts still another modification of the invention utilizing a more elaborate controllably flexible probe structure 162 to produce radiographs or fluoroimages, for medical or other purposes, of a kind which have not heretofore been obtainable. In particular, visual images may be obtained of only a portion of the total thickness of a living subject so that the image of a region of interest will not be obscured by superimposed images of other portions of the subject as is necessarily the case where both the X-ray source and the X-ray sensitive means are situated outside the body. The mechanism is shown in FIG. 8 as used for obtaining a radiograph of a portion of the spinal column of a subject 29c without there being an image of the subjects's rib cage superimposed upon the desired data. In the position shown in FIG. 8, another view may also be obtained which displays a portion of the subject's abdomen without there being superimposed images of the vertebra or other bony structrure such as the scapula.

This embodiment of the invention makes use of a modified endoscope 163 of the form having control structure 164 at one end from which a long narrow controllably flexible probe element or fiberscope 166 extends for insertion into various existing body openings of a medical patient 29c or into surgical incisions made for that purpose. Referring now to FIGS. 9, 10 and 11 in conjunction, endoscopes 162 have heretofore been used for visually inspecting interior regions of a medical patient through an eye piece 167 at the control end of the endoscope which is optically coupled to a light pipe 168 extending along the length of the probe to an objective lens 169 mounted in the opposite end 166. Such endoscopes customarily have an additional light pipe 171 extending along the length of the probe for illuminating the interior of the medical patient and also have a hollow passage 172 terminating at a fitting 173 at the control end through which fluids may be transmitted to the interior of the patient or drained therefrom. As adapted for usage in the present invention, the end 166 of the endoscope is provided with an additional light pipe 174 and the scintillation crystal 28 which constitutes the radiation sensitive element of the X-ray detector is situated at the end of the probe in optical contact with light ipe 174 behind an opaque disk 176 which blocks ambient light from the crystal. Endoscopes are customarily provided with an adjustable knob 177 which may be shifted to controllably flex the end of probe 166 in a first direction and a crank 178 for controllably flexing the probe in a tranverse direction so that the tip of the probe may be guided through convoluted passages within the patient's body. The controls for flexing the probe 166 are not further described herein inasmuch as the known mechanisms heretofore used for this purpose are fully adaptable to use with the present system without necessarily being modified.

Referring now to FIG. 12, the light pipe 174 separates from the probe 166 near the control end of the endoscope and enters the housing 109c of the X-ray detector 12c and is optically coupled to the photomultiplier tube 106c therein whereby visible light airsing from interaction of X-rays with the scintillation crystal 28 is transmitted to the photomultiplier tube and initiates output signals in the manner previously described. To prevent degradation of the detector signals from extraneous light, a light opaque sheath 179 surrounds the light pipe 174 between the probe end 166 and photomultiplier tube 106c.

In operation, with reference again to FIG. 8, an X-ray image of the medical patient 29c is obtained by inserting the probe end 166 into an appropriate opening in the body to bring the scintillation crystal 28c to the position from which an X-ray image is desired to be taken. To avoid injury to the patient, the previously described endoscope controls are carefully manipulated during the insertion process as is understood within the medical arts. An X-ray source 11c, which may be similar to that previously described, is then positioned adjacent the patient's body to direct X-rays towards the scintillation crystal 28c through the region of interest. The source 11c and the detector 12c are electrically coupled to a control circuit console 152c including a display means 13c containing an electrical control system which may also be similar to that previously described whereby a visual image of the region of interest is produced on screen 37c. With the X-ray source 11c in the position shown in FIG. 8, a view of a portion of the spinal column of the patient is obtained without such view being obscured by a superimposed image of the frontal portions of the rib cage. By shifting the X-ray source to position 11c' a visible image of the upper abdomen may be obtained that is not obscured by bony structure. This need not necessarily require repositioning of the probe 166. While positioned in this manner, the endoscope 162 may be used for more conventional purposes such as vieweing the interior of the patient through eye piece 167. Light for illuminating the interior of the patient for this purpose may be provided by a suitable source 181 coupled to the control end of the endoscope in the conventional manner through an additional light pipe 182. Again, it will be apparent that the system of FIG. 8 is useful for a variety of purposes other than medical diagnostic operations. The system may be used for example, to obtain an X-ray image of complex machinery, such as an aircraft engine, taken from a relatively inaccessible viewpoint within the interior of the engine.

The control circuit of the system was described with reference to FIG. 2 as adapted for a pulse mode of operation wherein discrete pulses resulting from individual X-rays intercepted by the detector are amplified and caused to control the brightness of particular points in the visual image. If, owing to the use of higher radiation flux levels, the count rate of the X-ray detector is too high to operate on an individual pulse basis without losses caused by pulse pile up, the control circuit may be adapted for operating on the basis of detector output current variations rather than on the basis of single counts. A suitable modification of the detector output circuit for this purpose is illustrated in FIG. 13. Photomultiplier tube 106d of the X-ray detector 12d may be of conventional construction and includes a photocathode 183 of the known form which emits electrons in response to visible light scintillations from the scintillation crystal 28d that result from X-ray interactions therewith. The output element is an anode 184 situated near the opposite end of the tube envelope 186 and electrons emitted from the photocathode are accelerated towards the anode by a series of spaced apart dynodes 187 which have progressively more positive voltages in the direction of the anode. The negative side of the detector high voltage supply 107d is coupled to photocathode 183 with the positive side of the side being grounded. To establish the desired operating voltages on the dynodes 187, dynode resistors 188 are connected in series between the negative side of voltage supply 107d and ground and each individual dynode is connected to the junction between a successive pair of the resistors 188. The output terminal 108d of the photomultiplier tube is connected to anode 184 and is connected to ground through a variable load resistor 189 which enables selection of the tube output signal voltage level.

The photomultiplier tube output terminal 108d is connected to one input of a broad band differential DC coupled amplifier 191 through the pre-amplifier 39b. The output of amplifier 191 is connected to one side of an integrating capacitor 192, which has the other side grounded, through a variable resistor 193 which enables selection of time constant of integration. The junction between variable resistor 193 an capacitor 192 is also connected to ground through a variable gain signal amplitude limiter amplifier 194 and the resistive element of the potentiometer 196. The signal for controlling beam intensity in the visual display means 13d is provided by connecting the Z terminal 38d of the display means with the adjustable voltage tap 197 of potentiometer 196. Potentiometer 196 enables adjustment of the signal voltage to match that required by the display means 13d. The base reference level of the signal supplied to the Z terminal of the display means 13d may be adjusted by means of another potentiometer 199 having a resistive element connected across a bi-polar DC voltage supply 201 and having an adjustable tap connected to the second input of amplifier 191.

Thus in the embodiment of FIG. 13, the brightness of each point in the visible image produced by display means is determined not by the presence or absence of an individual pulse but is instead dependent upon the magnitude of a signal originating from many X-rays received at scintillation crystal 28b as integrated by the capacitor 192. The general brightness level in response to a particular radiation flux level may be adjusted by means of variable resistor 193 and potentiometer 199. Limiter amplifier 194, which is operated in the saturated mode, acts to suppress the effects of abnormally large signals which may arise on occasion from extraneous sources such as a burst of cosmic rays.

Radiation dosage of the subject and uniformity of different regions of the visible image can be enhanced by providing automatic brightness control and FIG. 13 also illustrates additional circuit provision for this purpose. The degree of radiation transmissiveness of different regions of the subject may vary substantially. Regions of a medical patient containing bony structures, for example, are much more opaque to X-rays than is soft tissue. If the intensity of the X-ray beam impinging on the subject remains constant throughout the raster, then an undesirable variation of contrast in different portions of the visible image can be present. Bony regions may be too dark while soft tissue regions are too light. The automatic brightness control means of FIG. 13 acts to vary the X-ray intensity emitted by the source 11b in response to the average level of X-ray detection at different regions of the subject as necessary to minimize this problem. Other advantages of the automatic brightness control are reduced power consumption and longer X-ray source life. While the automatic brightness control system will be described as included in the system of FIG. 13, it is also equally applicable to the circuit of FIG. 1 which operates on a pulse basis.

Considering now suitable circuit provisions for automatic brightness control, the output terminal 108d of photomultiplier tube 106d is coupled to an integrating capacitor 202 through a pair of amplifiers 200 and 205 and variable resistor 203 which enables adjustment of the integration time constant. Amplifier 205 is of the differential form, referenced to an adjustable voltage source 210, for eliminating circuit noise. Thus, the voltage present on capacitor 202 at any given time is proportional to the average X-ray level received at scintillation crystal 28d during the immediately preceding time and will rise or drop if the average radiation flux which is being received at the scintillation crystal undergoes a change over a limited period of time. This voltage is transmitted to the control grid 47d of the X-ray source 11d through a differential DC operational amplifier 204, an optical coupler 206 and a driver amplifier 205 so that it provides a control grid voltage relative to the cathode voltage supplied by the main high voltage supply 62. This has the effect of automatically decreasing the intensity of the X-ray output of source 11d when the general radiation flux level at scintillation crystal 28d rises for a period of time and of increasing the X-ray output of the source when the radiation flux intercepted by crystal 28d decreases for a period of time as occurs when a denser region of the subject is being scanned. The optical coupler 206 serves to isolate the above described automatic brightness control circuitry from the high voltage at the cathode end of the X-ray source. To enable adjustment of the overall brightness level of the visible image, the other input of the differential amplifier 204 is connected to the adjustable tap of a potentiometer 207 having a resistive element connected across another bi-polar DC power supply 208.

Figure 14:
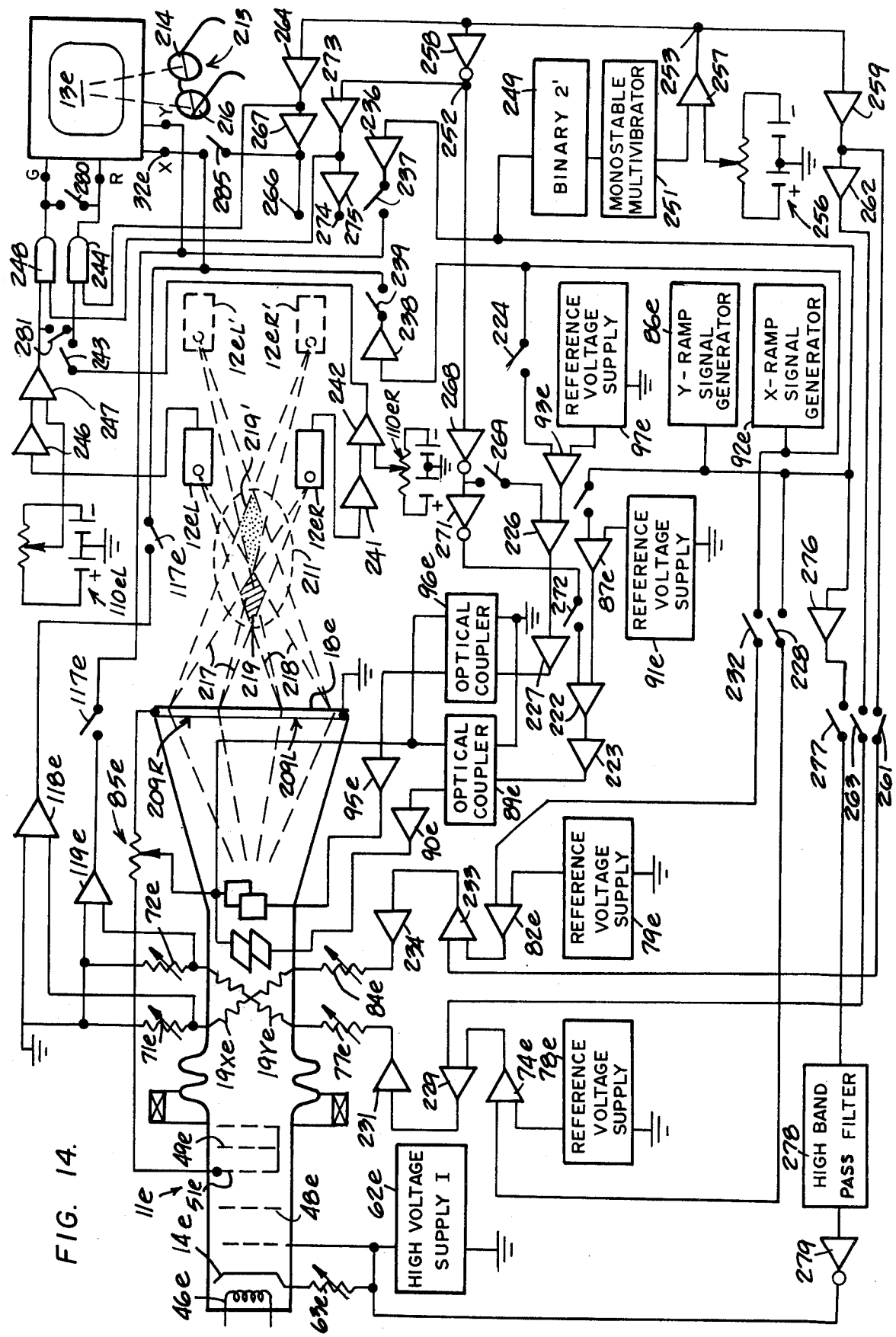
FIG. 14 illustrates a modification of the X-ray scanning system for producing stereoscopic or three dimensional images of the subject.

The embodiments of the invention described above produce visible images which are X-ray shadowgraphs in which all regions of the subject intervening between the X-ray source and the detectors appear in the image as if all such regions occupied a single flat image plane. The viewer of the two dimensional image cannot discriminate between different regions of the subject on the basis of depth other than from deduction based on prior knowledge of the general configuration of the subject. It is much more helpful in many situations to create a three dimensional image in which the observer can determine depth. One adaptation of the invention for producing a stereoscopic visible image of this kind is depicted in FIG. 14. Further, the system of FIG. 14 provides for viewing only a selected region of the subject in three dimensional form while the remainder of the image appears flat to the observer. The observer may control the size and shape of the region of the subject which he wishes to view in three dimensions.

The X-ray source 11c for the stereoscopic image system of FIG. 11 may be identical to that previously described except for the electron beam deflection control. Accordingly, to avoid unnecessary complication, the control system for the source 11c will not be redescribed except insofar as modifications are required to provide for the stereoscopic mode of operation.

By means of modified deflection control circuits which will hereinafter be described, the electron beam in source 11e is caused to alternately sweep through two separate rasters 209R and 209L on the face of the target plate 18e. While in some instances, the rasters 209R and 209L may overlap, the two rasters are spaced apart on target plate 18e in this example for reasons which will be discussed.

A pair of small area radiation detectors 12eR and 12eL are situated on the opposite side of the subject 211 from source 11e and are spaced apart in the same direction as the raster patterns 209R and 209L are spaced apart. Detectors 12eL and 12eR may be similar to the detector previously described and thus each has an output signal conductor 212L and 212R respectively at which electrical pulses are produced in response to the impingement of X-rays on the sensitive area of the detector. Detector 12eR is gated on, by means to be described, only during the period that raster pattern 209R of the source is being scanned, while detector 12eL is gated on only during periods when raster pattern 209L is being scanned. The visual display 13e is a color cathode ray tube having a scan pattern synchronized with that of the source 11e so that the display means completes a raster for each successive raster 209R or 209L of the source. To provide the desired three dimensional image, the output of X-ray detector 12eR is coupled to the display 13e, by means to be described, to control the intensity of the red color component of the visible image while the output of detector 12eL controls the green color component of the image. The visual display 13e is viewed by means such as a pair of eye glasses 213 which allow the red image on the display to reach only one eye of the observer while the green image reaches only the other eye of the observer. Thus, eye glass 213 may have one lens 214 formed of material transmissive only to red light wave lengths while the other lens 216 is formed of a material transmitting substantially only green wave lengths. Preferably the lower portion of each such lens is formed of clear glass to enable the observer to view the subject and the system or other objects without removing the eyeglasses. The observers biovisual system blends the red and green images into a single image perceived in shades of black and white.

One eye of the observer receives the view of the region of the subject which lies within the convergent path bounded by dashed lines 217 in FIG. 14 while the other eye receives an image of the region bounded by dashed lines 218. The portion 219 of the subject situated where these two regions intersect is perceived by the observer in three dimensions since each eye of the observer receives a separate image thereof taken from spaced apart positions. Although these images are separated in time and alternate, the well known persistence of vision effect causes the observer's biovisual system to blend the separate images into the single three dimensional image provided the rate of image alternation is more than a few cycles per second. To avoid flicker perception, the image alternation should preferably exceed about 25 cycles per second. However, the image data may be obtained at a slower scan rate and recorded on the previously described video tape recorder for playback at a higher rate.

It is not necessary to shift the subject 211 in order to change that portion of the subject which is seen in three dimensions. The three dimensonal portion of the image may be varied by shifting the detectors 12e L and 12e R towards the source 11e or away therefrom, for example to the position depicted at 12eL' and 12eR', at which a different region 219' is then imaged in three dimensions. Alternately, the source 11e may be moved while the detectors remain stationary. The subject may be rotated or shifted vertically or horizontally to obtain three dimensional images of still other regions or the source and detectors may be moved as a unit for this purpose. This capability is particularly useful for tomographic studies and particularly for medical tomography of the brain without the use of contrast agents. In selecting the direction of raster separation at the target plate of the source relative to the subject, it is usually desirable to scan at right angles to predominant structural lines in the subject. Thus in a medical chest X-ray, scanning across the subject's ribs rather than in a direction parallel to the ribs is usually preferable.

Considering now modifications of the control circuit for realizing the stereoscopic image production described above, X and Y deflection signals for source 11e are basically generated by a Y ramp signal generator 86e and an X ramp signal generator 92e which produce sawtooth wave forms. Utilizing electrostatic beam deflection in the source 11e, the output of Y ramp signal generator 86e is transmitted to one input of a differential amplifier 87e through a switch 221. The other input of amplifier 87e is provided with an adjustable reference voltage from a suitable source 91e to determine the base level of the deflection voltage and to thereby determine the position of raster 209R at the source. For this purpose, the output of amplifier 87e is coupled to one input of an additional differential amplifier 222 having an output coupled to a final deflection voltage amplifier 223 which is in turn coupled to the Y deflection plate 52e of the X-ray source through an optical coupler 89e and driver amplifier 90e. The other input of amplifier 222 is gated on and off by means to be described to extinguish raster pattern 209R during the periods when the alternate raster pattern 209L is being scanned. Similarly, the output of the X ramp signal generator 92e is transmitted to one input of a differential amplifier 93e through a switch 224 and another adjustable reference voltage supply 97e is coupled to the other input of amplifier 93e. The output of amplifier 93e is coupled to one input of a gating differential amplifier 226 having an output coupled to a final deflection voltage amplifier 227. The output of amplifier 227 is coupled to the X deflection plate 53e of of the source through another optical coupler 96e and driver amplifier 95e.

If the magnetic deflection system is to be employed in the source 11e, either separately from the electrostatic deflection system or in combination therewith, the output of Y ramp signal generator 86e is transmitted to one input of a differential amplifier 74e through a switch 228 and an adjustable reference voltage supply 78e is coupled to the other input of amplifier 74e. The output of amplifier 74e is coupled to one input of a gating amplifier 229 having an output coupled to one end of the Y deflection coils 19Ye through a final deflection current amplifier 231 and variable resistor 77e. The output of X ramp signal generator 92e is coupled to one input of a differential amplifier 82e through a switch 232 and the other input of amplifier 82e is coupled to an adjustable reference voltage supply 79e. The output of amplifier 82e is connected to one input of a gating amplifier 233 having an output coupled to one end of the X deflection coil 19Xe of the X-ray source through a final deflection current amplifier 234 and variable resistor 84e.

In order to synchronize the scanning action of the display 13e with that of the X-ray source 11e, when using electrostatic deflection in the source, the output of Y ramp signal generator 86e is transmitted to the Y sweep frequency terminal 31e of the display through an amplifier 236 and a switch 237. Similarly, the output of X ramp signal generator 92e is transmitted to the X sweep frequency terminal 32e of the display through another amplifier 238 and a switch 239. Amplifiers 236 and 238 are adjustable to match the voltage level supplied by the ramp signal generators with that required at the X and Y sweep frequency terminals of the visual display. Synchronization of the raster patterns of the X-ray source and visual display may be accomplished when using magnetic deflection in the source in that an amplifier 119e has inputs connected across variable resistor 72e through which the Y deflection coil 19Ye of the source is connected to ground while another amplifier 118e has inputs connected across another variable resistor 71e which is itself connected between the X deflection coil 19Xe and ground. Switches 117e provide for connection of the outputs of amplifiers 119e and 118e with the Y and X terminals 31e and 32e respectively of the visual display. Adjustment of the variable resistors 71e and 72e enables the basic level of the X and Y signals supplied to the visual display to be adjusted as necessary.

Output signals from X-ray detector 12eR are transmitted to the red intensity control terminal of display 13e through a pre-amplifier 241, a final differential amplifier 242, a switch 243 and an AND gate 244. Output signals from the other X-ray detector 12eL are transmitted to the green intensity control terminal of the display through a pre-amplifier 246, a final differential amplifier 247 and another AND gate 248. The AND gates 244 and 248 are controlled by means to be hereinafter described and function to alternately suppress each colored image while the other colored image is being displayed.

Gating of the X-ray source deflection controls to cause alternate scanning of raster patterns 209R and 209L and gating of the AND gates 244 and 248 to cause alternate display of the corresponding red and green images, is provided for by a scale of two binary counter 249 having an input coupled to the output of Y ramp signal generator 86e. The binary output signal controls a one-shot multivibrator 251 which produces a square pulse having a duration slightly more than that of the ramp signal duration. The output of the multivibrator 251 is applied to one input of a differential amplifier 257. The other input of differential amplifier 257 is set at a voltage obtained from a variable voltage supply 256 which voltage is equal to about one-half of the amplitude of the one-shot pulse. The output of the differential amplifier 257 at terminal 253 is thus a bipolar square wave which alternately changes polarity with each consecutive ramp pulse. Another terminal 252 is connected to terminal 253 through an inverting amplifier 258 and thus the polarity of the signal at terminal 252 is always the inverse of the polarity of the signal at terminal 253. The output of terminal 253 of amplifier 257 constitutes the red gate signal terminal 253 while the output terminal 252 of inverter 258 constitutes the green gate signal terminal.

The red gate signal terminal 253 is coupled to a second input of the previously described differential amplifier 229 of the source magentic deflection control through an amplifier 259 and switch 261 and is coupled to the second input of the previously described differential amplifier 233 of the magnetic deflection control system through amplifier 259, an additional amplifier 262, and another switch 263. The red gate signal terminal 253 is also coupled to the second input of the previously described AND gate 244 through an amplifier 264 and also to a terminal 266 through amplifier 264 and an additional amplifier 267.

The green gate signal terminal 252 is coupled to the second input of the previously described differential amplifier 226 of the electrostatic deflection control system of the X-ray source through an amplifier 268 and a switch 269 and is also coupled to the second input of the previously described differential amplifier 222 of the electrostatic deflection control system through amplifier 268 and an additional amplifier 271 and switch 272. The green gate signal terminal 252 is further coupled to the second input of the previously described AND gate 248 through an amplifier 273 to gate the green image on and off of display 13e and is also coupled to a terminal 274 through amplifier 273 and an additional amplifier 275.

The above described gating circuit operates to cause the source 11e to alternately scan the two separate raster patterns 209R and 209L while causing the visual display 13e to display the red image while raster pattern 209L is being scanned and to alternately display the green image while raster pattern 209R is being scanned. When the magnetic deflection system is used at the X-ray source 11e, signals from the red gate signal terminal 253 pass through the isolation amplifier 259 and switch 261 to the input of differential amplifier 233 and also pass through amplifier 259 and the additional isolation amplifier 262 and switch 263 to the second input of differential amplifier 229. The red gate signal thus changes the current transmitted through magnetic deflection coils 19Xe and 19Ye to cause the area of target plate 18e scanned by the electron beam of the source to shift in the X and Y directions by amounts determined by the amplitude of the red gate signal and the gains of the two amplifiers 259 and 262 which are adjustable. The angle of separation of the two raster patterns 209R and 209L is determined by adjusting the gains of the two amplifiers 262 and 259 relative to each other. The initial position or reference position of the raster before being displaced in the above manner is determined by the amplifiers 74e and 82e which compare the output voltages from reference voltage supplies 78e and 79e with the voltage levels of the Y ramp signal and X ramp signal respectively provided that switches 232 and 228 are closed.

If it is desired to use solely electrostatic deflection to control the raster displacements within the source 11e, switches 232, 117e and 228 are opened and switches 221 and 224 are closed. Also switches 261 and 263 are opened and switches 269, 237, 239 and 272 are closed. Under these conditions, the gating signals at the green gate signal terminal 252 pass through isolation amplifier 268 and switch 269 to differential amplifier 226 and also pass through amplifier 268 and an additional isolation amplifier 271 and switch 272 to differential amplifier 222. As amplifiers 268 and 271 are signal inverting amplifiers, the green gate signal causes the raster pattern of source 11e to shift in the negative X and Y directions by amounts determined by the amplitude of the green gate signal and the gains of amplifiers 268 and 271. The angle of shift of the source raster areas from the reference level is determined by the relative value of the gains of the two amplifiers 268 and 271. The initial or reference position of the raster, before being shifted as discussed above, is determined by the amplifiers 87e and 93e which compare the output voltages from reference voltage supplies 91e and 97e with the X and Y ramp signals if switches 221 and 224 are closed.

Using either the magnetic or electrostatic deflection system or both, the electron beam of X-ray source 11e is suppressed during the switching time required for raster shifting at the conclusion of each raster scan by differentiating the Y ramp signal from generator 86e to provide a gating pulse at the end of each raster scan. In particular, the Y ramp signal is passed through an isolation amplifier 276 and switch 277 to a high band pass filter 278 which differentiates the Y ramp wave form to provide a short duration blanking signal which is then applied to the control grid 47e of source 11e through an inverting amplifier 279. As the inverted signal is negative, the electron beam from cathode 14e is temporarily suppressed.

The above described system is but one example of an adaptation of the invention to the production of three dimensional or stereo images. For example, instead of utilizing red and green images for transmission to separate eyes of the observer, two side-by-side images of the same color or colors may be established at the display 13e by shifting alternate raster patterns thereat in essentially the same manner that the raster patterns are separated and alternated within the source 11e. The display 13e may then be viewed by the observer through suitable known means which transmit one of the side-by-side images to one eye only while transmitting the other of the side-by-side images to the other eye only. This mode of operation may be accomplished by closing switch 280 to provide a single color and switch 285 to transmit raster shifting signals to the X sweep frequency terminal 31e of the display through isolation amplifier 267. As another technique, side-by-side separate images for stereo viewing by separate eyes may be established by utilizing two separate side-by-side displays 13e which are alternately gated on and off in synchronism with the shifting between rasters 209R and 209L at the source.

Figure 15:
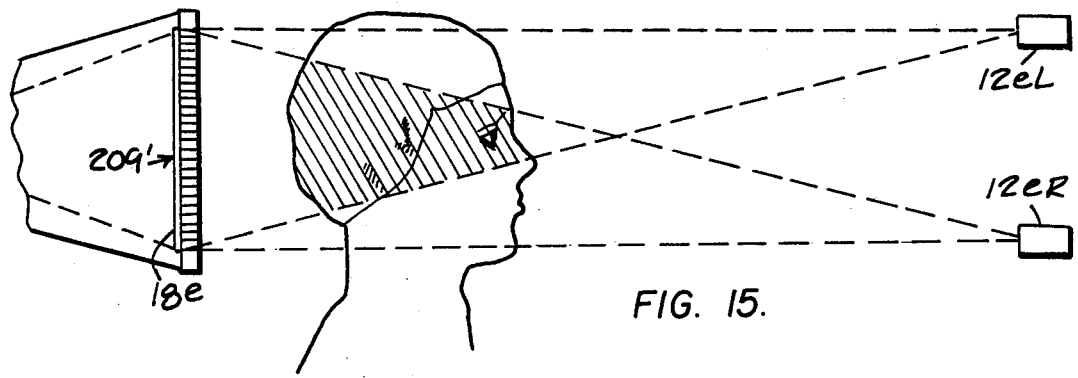
FIG. 15 illustrates a modification of the stereoscopic image producing system.

The system of FIG. 14 provides for spaced apart alternate raster patterns 209R and 209L on the target plate 18 of the X-ray source in order to produce a visible image wherein only certain selected regions of the subject such as regions 219 and 219' appear in three dimensions in the visible image while the remainder of the subject is seen in two dimensional form. However, the system may also be utilized to obtain a visible image in which substantially all observed portions of the subject appear in three dimensional form. This may be accomplished by opening switches 261, 263, 269 272, 280 and 285, thereby blocking the raster shift signals from the X-ray source 11e. As shown in FIG. 15, successive raster patterns at target plate 18e of the X-ray source will then all occur at the same broad area 209' thereof. However, the visible image is still perceived in three dimensional form as the rapidly alternating red and green images arise from separate spaced apart view points defined by detectors 12eL and 12eR.

Figure 16:
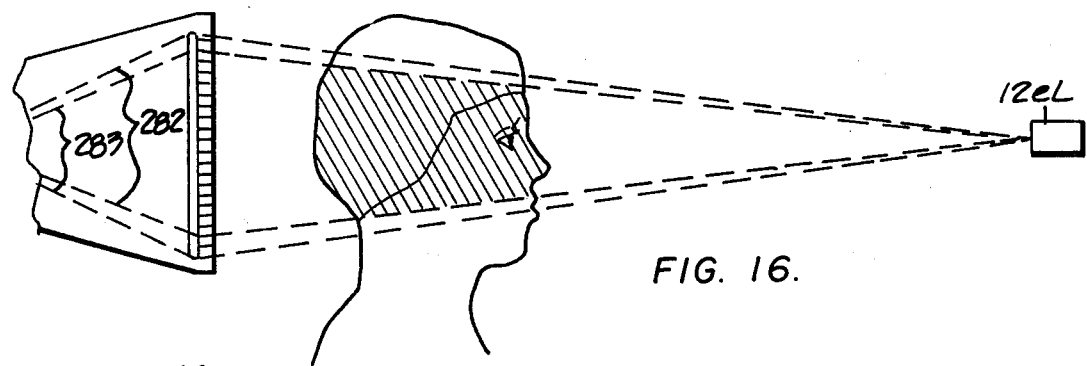
FIG. 16 illustrates another modification of the stereoscopic image producing system.

The three dimensional visible images may be obtained with only a single X-ray detector. Referring again to FIG. 14, this may be accomplished in the example of the invention depicted therein by opening switch 243 thereby isolating detector 12eR from the red image modulation terminal of receiver 13e. An additional switch 281 is then closed so that the image intensity signals originating from a single detector 12eL are transmitted to both the red and green image modulation terminals of the display, the switches 261 and 263 or the switches 269, 272 or both sets of switches being closed so that displacement of alternate rasters in the source 11e is again established. These displacements are adjusted by the means previously described for that purpose so that there is only a relatively small displacement between alternate raster patterns on the target plate 18e of the X-ray source. As depicted in FIG. 16, the raster patterns 282 which take place during the period the red image system of the display is gated on are only slightly displaced from the raster patterns 283 which occur during the period that the green image system of the display is gated on. Thus, in the system of FIG. 16, three dimensional data is introduced into the visual image by making use of a single X-ray detector 12eL alternately receiving X-radiation from two at least partially spaced apart raster areas, whereas in the system of FIG. 15, the three dimensional data was obtained by using a pair of spaced apart X-ray detectors each receiving X-radiation from a single raster area at the source.

Figure 17:
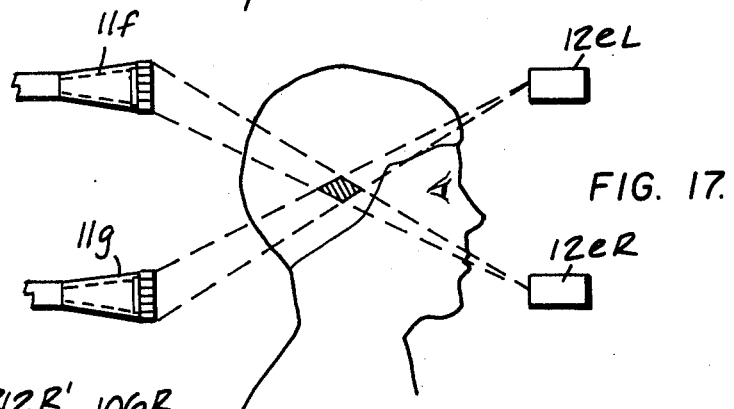
FIG. 17 depicts still another modification of the invention as adapted for the production of stereoscopic images.

While various arrangements have been described above for producing three dimensional visible images utilizing a single X-ray source 11, it is also possible to utilize a pair of separate sources 11f and 11g as depicted in FIG. 17 wherein each such source alternately scans the subject. Shifting of the raster pattern within either individual one of these sources is unnecessary. A control circuit essentially similar to that depicted and described with reference to FIG. 14 may be used to control both sources 11f and 11g by opening switches 261, 263, 269, 272 and 277 to inactivate the raster shifting components and blanking circuits and by connecting the terminals 266 and 274 to individual ones of the control grids of the two X-ray sources of FIG. 17.

While the stereo system control circuit of FIG. 14 has been described as embodying a variety of components intended to allow for adaptation to the differing X-ray sources and modes of operation depicted in FIGS. 15, 16 and 17, it will be apparent that portions of the control circuit may be eliminated if only one such mode of operation is contemplated. For example, in a system designed to operate only in the mode of operation depicted in FIG. 15 wherein shifting of the raster pattern at the X-ray source is not required, the raster pattern displacement components of FIG. 14 need not be present. In a system designed to utilize the single X-ray detector method of FIG. 16, the circuit components associated with the additional detector 12eL may be eliminated.

Figure 19:
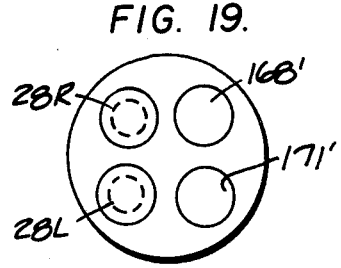
FIG. 19 is a probe end view of the endoscope apparatus of FIG. 18.
Figure 18:
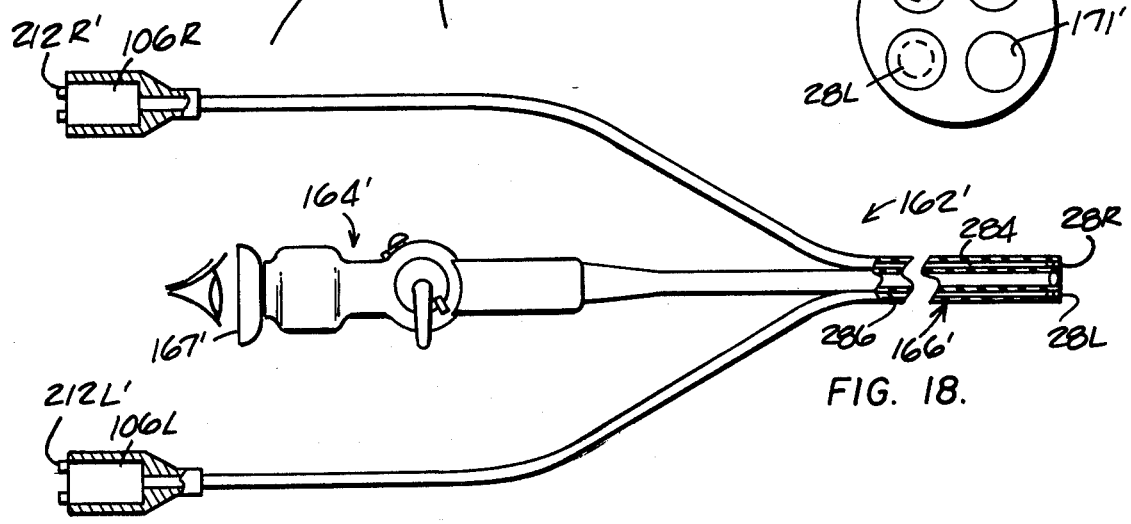
FIG. 18 depicts a modification of the endoscope apparatus of FIG. 9 for use in a stereoscopic imaging producing system.

An endoscope device for utilizing the present invention in medical or other applications, where it is desired to position the X-ray detectors within constricted areas, has been previously described with reference to FIGS. 8 to 12. Referring now to FIGS. 18 and 19, modifications of the endoscope 162' are shown to enable usage with those of the three dimensional image producing systems described above in which two spaced apart detectors are required. While the two separate ones of the previously described endoscopes may be employed for this purpose, the modified endoscope mechanism depicted in FIGS. 18 and 19 may facilitate operations in that it requires insertion and guiding of only one probe into the subject. Endoscope 162' may have a controllably flexible probe end 166' manipulatable through control structure 164' at the other end essentially as previously described and may have a light pipe 171' for transmitting light into the interior of the subject and another light pipe 168' extending along the probe 166' whereby the interior of the subject may be viewed through an eye piece 167' at the control end, the detailed structure being similar to that previously described. The stereoscopic endoscope 162' differs from that previously described in that two spaced apart radiation sensitive scintillation crystals 28R and 28L are mounted at the flexible end of the probe. Crystals 28R and 28L are optically coupled to a separate one of a pair of light pipes 284 and 286 which extend within the probe end 166' and separate therefrom to couple to separate photomultiplier tubes 106R and 106L having signal output terminals 212R' and 212L'. Terminals 212L' and 212R' may be coupled to the amplifiers 246 and 241 of the control circuit previously described with reference to FIG. 14.

With the flexible end 166' of the probe inserted into the subject, three dimensional images may then be produced in the manner described with reference to the system of FIG. 14. If desired, provisions for adjustment of the separation of the two scintillation crystals 28R and 28L on probe end 166' may be included to enable variation of the extent of the three dimensional effect.

While the invention has been described with respect to certain preferred embodiments, it will be apparent that many other modifications and variations are possible and it is not intended to limit the invention except as defined in the following claims:

What is claimed is:

1. A scanning X-ray source having a vacuum envelope with a cathode therein for producing electrons and having a broad anode structure spaced from said cathode and positioned to receive electrons therefrom and having means for directing a narrow electron beam from said cathode to said anode structure for producing X-rays by impact of electrons on said anode structure, said X-ray source further having beam deflection means between said cathode and anode structure for sweeping said electron beam across said anode structure to establish a moving point source of X-rays thereat, said anode structure comprising:

a thin first layer of metallic anode material facing said cathode to receive said electron beam and producing said X-rays in response to electron impact on said first layer, and a second layer of backing plate material extending parallel to said first layer and forming at least part of a high strength end wall of said vacuum envelope, said second layer of backing plate material being thicker than said first layer of anode material and being formed of a substance of lower atomic number than the metal of said first layer.

2. A scanning X-ray source as defined in claim 1 wherein said thin first layer of anode material is bonded to said second layer of backing plate material and support thereby.

3. A scanning X-ray source as defined in claim 1 wherein said anode structure further comprises a reinforcing member disposed against the surface of said second layer which is furthest from said first layer, said reinforcing member being formed of X-ray transmissive material.

4. A scanning X-ray source as defined in claim 3 wherein said reinforcing member is a honeycomb structure having spaced-apart hollow openings therein.

5. A scanning X-ray source as defined in claim 1 wherein said vacuum envelope is formed of electrically insulative material and has an exterior coating of electrically conductive material on the exterior surface at least at the portion of said exterior surface closest to said anode structure, said first layer of metallic anode material being electrically connected to said exterior coating of said vacuum envelope.

6. A scanning X-ray source as defined in claim 5 further comprising low resistance electrically conductive means for connecting said anode structure including said first layer of anode material and said exterior coating to ground.

7. A scanning X-ray source as defined in claim 1 further comprising a relatively thick collimator member disposed on the opposite side of said first layer of anode material and said second layer of backing plate material from said cathode, said collimator being formed of an X-ray absorbent substance of greater density than the backing plate material of said second layer and having at least one X-ray passage for transmitting X-rays which pass through said first and second layers to a predetermined location.

8. A scanning X-ray source as defined in claim 7 wherein said collimator has a plurality of said passages, said passages being spaced apart and being convergent in that all of said passages are directed towards a single point which is spaced apart from the anode end of said X-ray source.

9. A scanning X-ray source having a vacuum envelope with a cathode therein for producing electrons and having a broad anode structure spaced from said cathode and having means for directing a narrow electron beam from said cathode to said anode structure for producing X-rays thereat, said X-ray source further having beam deflection means between said cathode and anode structure for sweeping said electron beam across said anode structure to establish a moving point source of X-rays thereat, said anode structure comprising:

a thin first layer of metallic material facing said cathode to receive said electron beam and producing said X-rays in response to electron impact, a second layer of material extending parallel to said first layer and forming at least part of a high strength end wall of said vacuum envelope, said second layer being thicker than said first layer and being formed of a substance of lower atomic number than the metal of said first layer, a reinforcing member disposed against the surface of said second layer which is furthest from said first layer, said reinforcing member being formed of X-ray-transmissive material wherein said reinforcing member is a honeycomb structure having spaced-apart hollow openings therein, and a third layer of material disposed against the surface of said reinforcing member which is furthest from said second layer, said third layer being formed of a substance of lower atomic number than the metal of said first layer.

* * * * *

UNITED STATES PATENT OFFICE
CERTIFICATE OF CORRECTION

Patent No. 4,057,745    Dated November 8, 1977

Inventor(s) Richard D. Albert

It is certified that error appears in the above-identified patent and that said Letters Patent are hereby corrected as shown below:

Column 6, line 48 - "inaminate" should read --inanimate--.

Column 8, line 60 - after "detector", "to" should be deleted.

Column 12, line 21 - after "selectively", comma should be deleted.

Column 13, line 51 - before "images", "recorder" should read --recorded--.

Column 14, lines 57 and 67 - "bremmstrahlung" should read --bremsstrahlung--.

Column 15, lines 9 and 23 - "bremmstrahlung" should read --bremsstrahlung--.

Column 20, lines 33 and 37 - "11c" should read --11e--.

UNITED STATES PATENT OFFICE
CERTIFICATE OF CORRECTION

Patent No. 4,057,745          Dated November 8, 1977

Inventor(s) Richard D. Albert

It is certified that error appears in the above-identified patent and that said Letters Patent are hereby corrected as shown below:

Column 23, line 37 - "magentic" should read --magnetic--.

Column 24, line 43 - "X and Y" should read --Y and X--.

Signed and Sealed this

Twenty-second Day of January 1980

[SEAL]

Attest:

SIDNEY A. DIAMOND

Attesting Officer    Commissioner of Patents and Trademarks